US009446287B2

(12) United States Patent
Weast et al.

(10) Patent No.: US 9,446,287 B2
(45) Date of Patent: Sep. 20, 2016

(54) SENSOR-BASED ATHLETIC ACTIVITY MEASUREMENTS

(75) Inventors: Aaron B. Weast, Portland, OR (US); James M. Mullin, Bend, OR (US)

(73) Assignee: NIKE, Inc., Beaverton, OR (US)

( * ) Notice: Subject to any disclaimer, the term of this patent is extended or adjusted under 35 U.S.C. 154(b) by 1076 days.

(21) Appl. No.: 13/175,216

(22) Filed: Jul. 1, 2011

(65) Prior Publication Data

US 2013/0006583 A1    Jan. 3, 2013

(51) Int. Cl.
| | | |
|---|---|---|
| G01C 22/00 | (2006.01) | |
| H03F 1/26 | (2006.01) | |
| A63B 24/00 | (2006.01) | |
| A61B 5/11 | (2006.01) | |
| A61B 5/00 | (2006.01) | |

(52) U.S. Cl.
CPC ........... *A63B 24/0062* (2013.01); *A61B 5/112* (2013.01); *A61B 5/6807* (2013.01)

(58) Field of Classification Search
CPC .. A61B 5/681; A61B 5/6831; A61B 5/1038; A61B 5/1121; A61B 5/1123; G01C 22/006; G04C 21/025; G04C 21/02; A43B 23/24; A43B 3/0005; A43B 3/0031; A43B 3/0078; G01P 15/08; G01P 1/023; G01P 15/0922; A63B 2024/0065
USPC .......................................... 702/127, 160, 189
See application file for complete search history.

(56) References Cited

U.S. PATENT DOCUMENTS

| | | | |
|---|---|---|---|
| 6,882,955 B1 | 4/2005 | Ohlenbusch et al. | |
| 6,898,500 B2* | 5/2005 | Kobayashi | 701/48 |
| 6,898,550 B1* | 5/2005 | Blackadar | A43B 3/0005 |
| | | | 324/160 |
| 2005/0010139 A1* | 1/2005 | Aminian et al. | 600/595 |
| 2011/0288811 A1* | 11/2011 | Greene | 702/141 |
| 2013/0123665 A1* | 5/2013 | Mariani | A61B 5/1038 |
| | | | 600/592 |

FOREIGN PATENT DOCUMENTS

| | | |
|---|---|---|
| CN | 1272926 A | 11/2000 |
| CN | 101590315 A | 12/2009 |
| JP | 2009160392 A | 7/2009 |

(Continued)

OTHER PUBLICATIONS

International Search Report and Written Opinion for application No. PCT/US2012/044924 mailed Oct. 25, 2012.

(Continued)

*Primary Examiner* — An Do
(74) *Attorney, Agent, or Firm* — Banner & Witcoff, Ltd.

(57) ABSTRACT

Determining pace or speed based on sensor data may include determining an amount of contact time a user's foot has with a workout surface such as the ground. Contact time may be determined by identifying samples in the sensor data that correspond to various events such as a heelstrike, a toe-off and a subsequent heelstrike. In one example, these events may be identified by determining a sequence of three sample values (e.g., a triplet) that exceeds corresponding thresholds. The validity of an identified triplet (e.g., heelstrike, toe-off and heelstrike) may be confirmed by determining whether a difference between a last event sample and a middle event sample is greater than a difference between the middle event sample and an initial event sample. Once confirmed, a contact time may be determined from the triplet. A linear or non-linear relationship may then be applied to the contact time to determine a speed or pace.

17 Claims, 15 Drawing Sheets

(56) References Cited

FOREIGN PATENT DOCUMENTS

| JP | 2011056278 A | 3/2011 |
|---|---|---|
| WO | 9918480 A1 | 4/1999 |
| WO | 03/065891 A2 | 8/2003 |
| WO | 03065891 A2 | 8/2003 |
| WO | 2009152456 A2 | 12/2009 |

OTHER PUBLICATIONS

Jun. 18, 2015 Office Action issued in Canadian Patent Application No. 2840736.

* cited by examiner

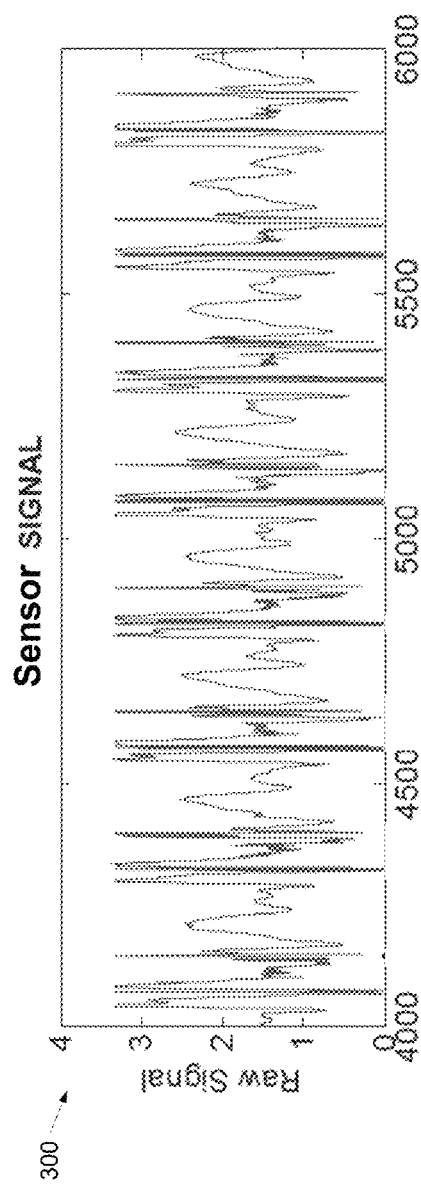
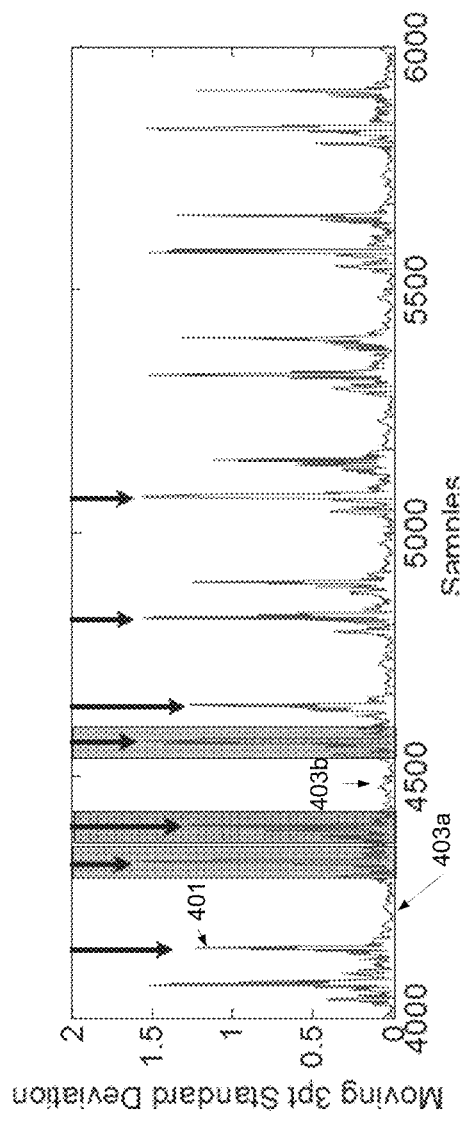

FIG. 9

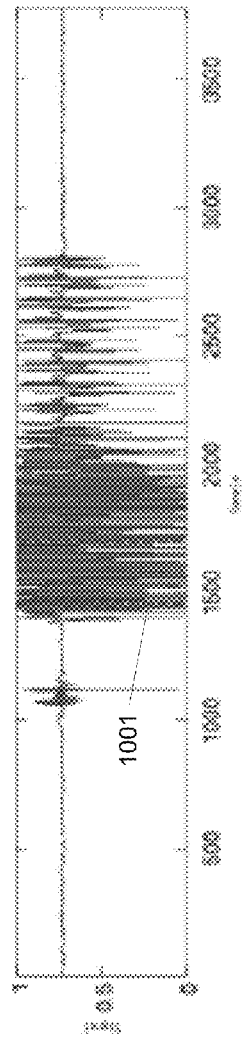
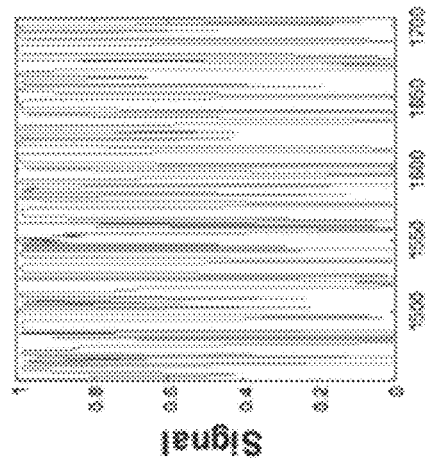
FIG. 10A
FIG. 10B

SENSOR-BASED ATHLETIC ACTIVITY MEASUREMENTS

TECHNICAL FIELD

The present invention generally relates to an athletic performance monitoring device and, more particularly, to determining athletic information based on sensor output and detection of foot-based events using signal processing.

BACKGROUND

With the increased focus on physical fitness and health, the popularity of athletic activity sensing devices has grown significantly in recent times. The use of athletic activity sensors provides individuals with the ability to concretely identify the amount of athletic activity performed. In running, jogging or walking, for example, individuals will often use pedometers or accelerometers to measure an amount of distance traversed, a number of steps taken, an amount of calories burned, a pace of the run and the like. In some current systems, accelerometers are used to determine an amount of contact time that a user's foot has with the ground to determine pace. For example, U.S. Pat. No. 6,493,652, entitled "MONITORING ACTIVITY OF A USER IN LOCOMOTION ON FOOT" describes some algorithms and methods for determining a user's pace based on contact time. However, current algorithms and methods by which the contact time and pace are determined can vary significantly in accuracy between different environments and between different users. Additionally, some accelerometer-based athletic activity measurement systems are only able to measure pace when a user is running or moving above a certain speed. Additionally, many of the current systems require frequent calibration and re-calibration in order to maintain accuracy of the measurements.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Aspects of the disclosure relate to the processing of foot-based sensor data to determine an amount of contact time a user's foot has with an exercise surface and to subsequently calculate a pace, distance, speed and/or other athletic metrics based thereon. In one example, determining a user's contact time may include determining where certain events such as a heelstrike and a toe-off exist in the sensor output. In a specific example, a processing system may identify triplets of events, each triplet including a first heelstrike, a toe-off and a subsequent second heelstrike. The consecutive (e.g., without intervening events) nature of the triplet allows the processing system to identify when a user has taken a step. Based on the timing of the various events of a triplet, a foot contact time may be calculated. Additionally or alternatively, contact time and corresponding triplets may be filtered if the contact time is a specified number of standard deviations away from the mean. Filtering allows the processing system to remove potential outliers or flawed data points prior to calculating pace and other athletic metrics.

According to another aspect, a fast fourier transform methodology may be used to determine contact time. In one example, a fast fourier transform may be performed on sensor output data. One of the frequency peaks resulting from the fast fourier transform may then be identified as corresponding to the contact time. The identification of the appropriate frequency peak may be based on empirical data and/or studies obtained from sample studies.

According to yet another aspect, an effort model or system may be used to determine contact time and subsequently speed and/or pace. Effort may be visually and mathematically correlated to the magnitude of the sensor output signal. Accordingly, the greater the magnitude of the signal, the greater the speed or pace of the user. A formula or algorithm may be derived to define the correspondence between the magnitude of the sensor output signal and the contact time and/or pace.

Other features and advantages of the invention will be apparent from the following examples in the specification taken in conjunction with the following drawings.

BRIEF DESCRIPTION OF THE DRAWINGS

FIG. 3 is a graph of example data received from a sensor according to one or more aspects described herein.

FIG. 4 is a graph of example standard deviations determined based on sensor output data according to one or more aspects described herein.

FIG. 9 illustrates a computer algorithm that may be used to perform a Fast Fourier Transform (FFT) on sensor output data according to one or more aspects described herein.

FIG. 10A illustrates example sensor output data according to one or more aspects described herein.

FIG. 10B illustrates a sample window of the example sensor output data of FIG. 10A.

DETAILED DESCRIPTION

Figure 1:
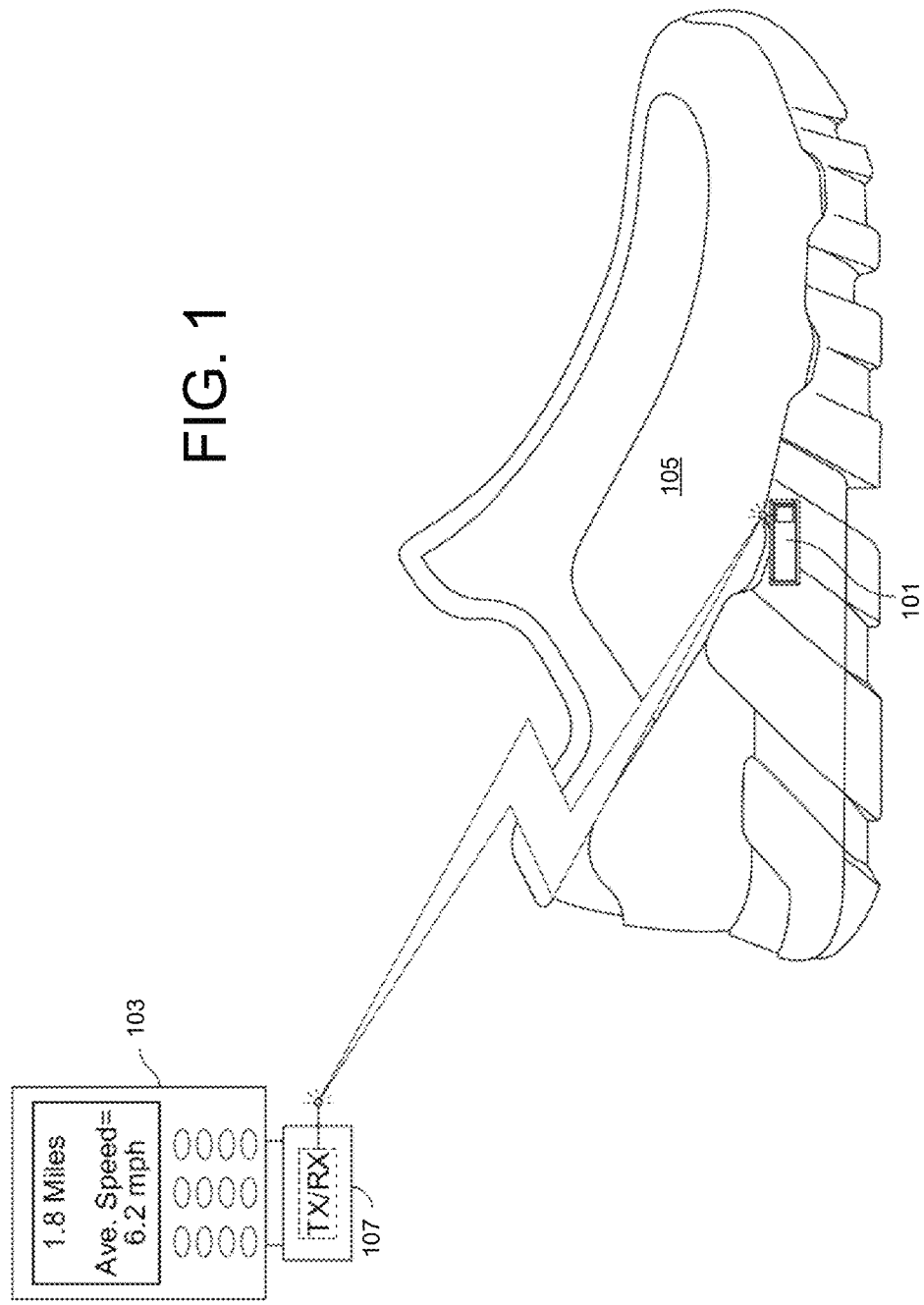
FIG. 1 illustrates an athletic activity monitoring system according to one or more aspects described herein.

While this invention is susceptible of embodiment in many different forms, there are shown in the drawings, and will herein be described in detail, preferred embodiments of the invention with the understanding that the present disclosure is to be considered as an exemplification of the principles of the invention and is not intended to limit the broad aspects of the invention to the embodiments illustrated and described.

FIG. 1 illustrates an example athletic activity system including a foot-mounted accelerometer-based sensor 101 and an information display device 103. Foot-mounted sensor 101 may be placed in a shoe or other type of footwear, attached to a user's foot or leg, attached to the footwear (e.g., on an exterior portion such as the shoelace or internal to a sole portion as shown with shoe 105) or the like. Sensor 101 includes a solid-state accelerometer that is configured to sense acceleration along multiple axes. For example, sensor 101 may include a six-axis accelerometer. Sensor 101 may further include a wireless transmitter and/or transceiver 107 that allows sensor 101 to wirelessly provide data to information display device 103. Transceiver 107 may be integrated into the display device 103 or may be a detachably connectable device. In some arrangements, sensor 101 may include a wired connector or connection in addition or alternatively to a wireless transmitter or transceiver as well as a storage medium (e.g., flash memory) to temporarily or permanently store data. In one example, sensor 101 may store measured data until a schedule transmission time or until receiving a request for the data (e.g., from information display device 103). Additionally or alternatively, sensor 101 may include other types of sensors including pressure-sensitive resistive switches, piezoelectric transducers, contact switches, mercury switches and the like.

Information display device 103 may include a wireless receiver and/or transceiver to receive data from and/or transmit data to sensor 101. For example, information display device 103 may receive sensor measurements from sensor 101 or transmit commands to sensor 101 (e.g., requesting data from sensor 101 upon manual user prompting). In one or more arrangements, information display device 103 may comprise a user-worn device such as a watch or other wrist worn devices, armband, chest strap, eyewear, headwear and the like. Information display device 103 may further include a processor, memory and other input/output components such as speakers, touchscreen input systems, microphones, haptic feedback devices, data ports, and connectors. The memory may store computer readable instructions' that are executable by the processor and device 103 to process sensor data from sensor 101. For example, in one arrangement, information display device 103 may calculate or otherwise determine pace, distance and/or calories burned based on signals and data received from sensor 101. Algorithms, methods and systems for making such determinations are discussed in further detail herein.

In one example method of operation, a user may start data recordation by pressing a button or otherwise inputting a command into information display device 103. In response, display device 103 may then begin polling sensor 101 for information and recording the data in storage. Display device 103 may further begin processing the data dynamically (e.g., in real-time) so that the processed information such as pace or distance may be displayed for the user's information in real-time. A user may further stop recordation and/or processing by inputting a corresponding command using display device 103. Recorded data may be automatically stored by the display device 103 for a predetermined amount of time or indefinitely depending on a default setting or a user's preferences. In some arrangements, data may also be transmitted wirelessly through a computer network such as the Internet to one or more remote databases, servers or other systems. For example, device 103 may transmit workout activity data to a remote athletic performance tracking site on the Internet.

In one or more configurations, data processing to generate performance metrics may be performed by a device (not shown) separate from information display device 103. For example, the processing may be performed by a separate processing device that interfaces with both sensor 101 and display device 103 and, in one particular example, acts as an intermediary between sensor 101 and display device 103. Such a processing device may be used in instances where display device 103 might not have appropriate communication capabilities (e.g., hardware, software, firmware) to receive data directly from sensor 101. Accordingly, the separate processing device may be configured to receive sensor data and communicate with sensor 101 and provide the information to display device 103 in a compatible manner. The processing device may be directly and physically connected to display device 103. Alternatively, the processing device may communicate with display device 103 through a wireless connection. Similarly, processing device may be physically connected to sensor 101 or wirelessly connected using near field communication protocols and technology, local area networks and/or wide area networks. In some instances, the processing device may comprise a remote or local server that provides data processing over a wide area network or local area network.

According to one aspect, sensor 101 may be configured to conduct at least some processing of the sensor data prior to transmitting the information to display device 103 or a separate processing device. For example, sensor 101 may detect movement through changes in measured voltage. To make the data more understandable or easier to process, sensor 101 may pre-process the voltage information into a value adhering to a predefined scale (e.g., an unsigned digital value between 0 to 255). Sensor 101 may further include storage systems such as FLASH memory and/or hard disk memory for storing sensor data for a predefined amount of time. For example, sensor data may be stored in sensor 101 for 10 days, until the memory is full, until a user elects to clear the memory and the like.

Figure 2:
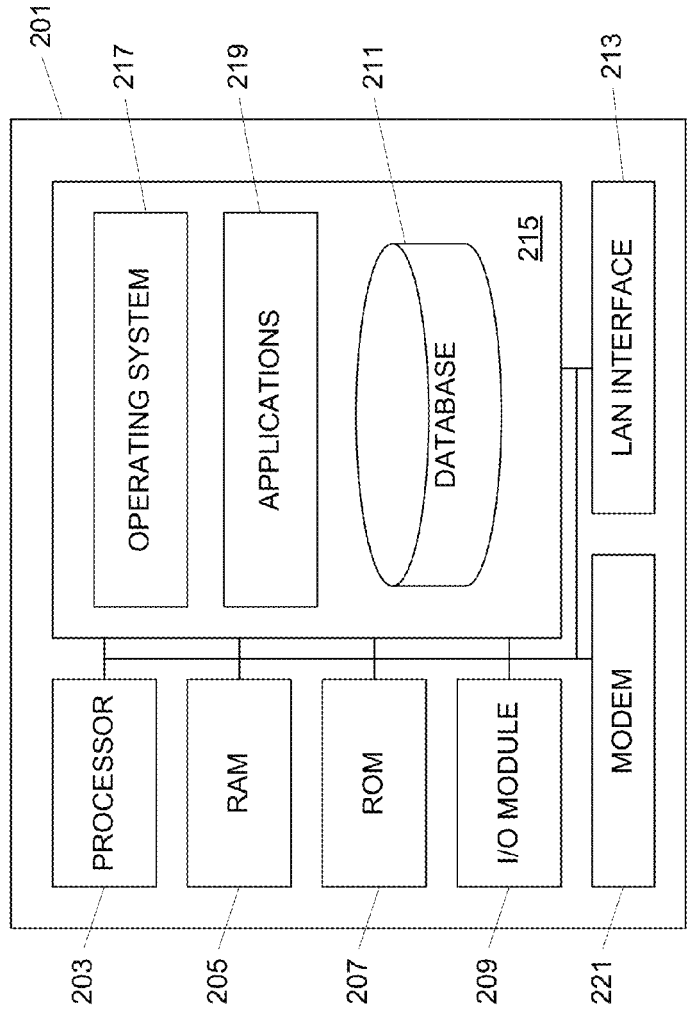
FIG. 2 illustrates a computing environment in which one or more aspects described herein may be used.

FIG. 2 illustrates a computing device that is operable to process a variety of data and perform a variety of functions. For example, computing device 201 may correspond to a sensor such as sensor 101 of FIG. 1, a processing device or system and/or an information display device such as device 103 of FIG. 1. In the block diagram of FIG. 2, computing system 201 may have a processor 203 for performing mathematical computations and controlling overall operation of the computing system 201 and its associated components, random access memory (RAM) 205, read-only memory (ROM) 207, input/output (I/O) module 209, and memory 215. I/O 209 may include a microphone, mouse, biometric scanner or identifier, keypad, touch screen, scanner, optical reader, and/or stylus (or other input device(s)) through which a user of computing device 201 may provide input, and may also include one or more of a speaker for providing audio output and a video display device for providing textual, audiovisual and/or graphical output. Software (e.g., computer readable instructions) may be stored within memory 215 and/or other storage to provide instructions to processor 203 for causing and enabling device 201 to perform various functions. For example, memory 215 may store software used by the computing system 201, such as an operating system 217, application programs 219, and an associated database 211. Alternatively, some or all of computing device 201 may be embodied in hardware or firmware (not shown). In one or more arrangements, computing device 201 may include one or more built-in sensors such as an accelerometer as described with respect to sensor 101 of FIG. 1, a heart-rate sensor, pressure sensor and the like.

Computing device 201 may also operate as a mobile communication device or terminal (e.g., mobile phones, PDAs, notebooks, etc.) that includes various other components, such as a battery, speaker, and antennas (not shown). Additionally or alternatively, computing device 201 may be connected to one or more networks through modem 221 or local area network (LAN) interface 213. In one or more examples, computing device 201 may have wired or wireless connections to one or more networks including BLUETOOTH connections, cellular communication connections, satellite connections and/or combinations thereof FIG. 3 illustrates an example graph of data that may be output by a sensor such as sensor 101 of FIG. 1. The graph 300 corresponds to a user's running activity and represents a data sampling rate (e.g., sampling voltages detected by the sensor) of 400 samples per second with a raw signal scale of 0-4. A user's stride, either in walking, jogging or running, may include several known events such as a heelstrike (e.g., when a user's heel strikes the ground) followed by a toe-off (e.g., when a user's toe leaves the ground). In between the user's heelstrike and toe-off, the user's foot is generally in contact with the ground. By determining the foot ground contact time, a user's pace or speed may be determined. However, determining when a user's heel strikes the ground and when the user's toe lifts off the ground may be difficult solely based on the raw signal output. As illustrated, the sheer number of: peaks and valleys in graph 300 makes it difficult to identify particular events (e.g., heelstrikes and toe-offs). Algorithms for converting or processing the raw signal output into a more useable form and subsequently calculating an amount of foot contact time, a user's pace and/or speed exist. However, as discussed above, current algorithms and methods may vary significantly in accuracy depending on the type of movement exhibited by the user. For example, some algorithms may result in inaccurate contact times and thus, inaccurate speeds and distances, during sprint exercises (versus slower running or walking). Other algorithms may have difficulty in processing walking exercises to determine accurate paces, speeds and/or distances.

The present disclosure uses pre-processing of the raw signal using a rolling 3 point standard deviation formula to identify more accurately the various stepping events (i.e., heel strikes and toe offs). For example, the following formula may be used to process the raw signal output as shown in graph 300 of FIG. 3:

$$\sigma_i = \sqrt{\left(\frac{1}{N}\sum_{i=1}^{i+1}(x_i - \bar{x}_i)^2\right)}$$

$$N = 3$$

In the above equation, N is a constant and represents the number of samples being used to determine the standard deviation while x represents the value of the raw signal output. In the above example, 3 samples (i.e., N=3) are being analyzed for each sample number or time i. The algorithm uses the immediately previous, current and immediately subsequent samples to determine the standard deviation corresponding to the current sample. In particular, the algorithm sums the squared difference between each of the three samples and the mean of the three samples. The sum is then divided by the number of samples N. The standard deviation is then calculated by taking the square root of the value resulting from the previous calculations. A three-point standard deviation for each sample may be calculated and subsequently graphed.

FIG. 4 is an example graph of standard deviation versus sample/time generated based on the three-point standard deviation algorithm described above as applied to the raw signal data of FIG. 3. By pre-processing the raw signal (e.g., before analyzing the signal for toe-off or heelstrike events), the heelstrike (h.s.) and toe-off (t.o.) events may be more easily identified. For example, peaks such as peak 401 may be more pronounced or more significant in magnitude relative to non-peak portions of the graph such as areas 403a and 403b. Accordingly, peaks that correspond to a heelstrike or toe-off event may be more readily discernible from peaks not corresponding to such events. In some arrangements, only those peaks that reach a certain magnitude (e.g., standard deviation) may be analyzed to determine if those peaks correspond to a heelstrike or toe-off event. Those peaks that do not meet the threshold magnitude may be filtered out or ignored during the analysis.

Figure 5:
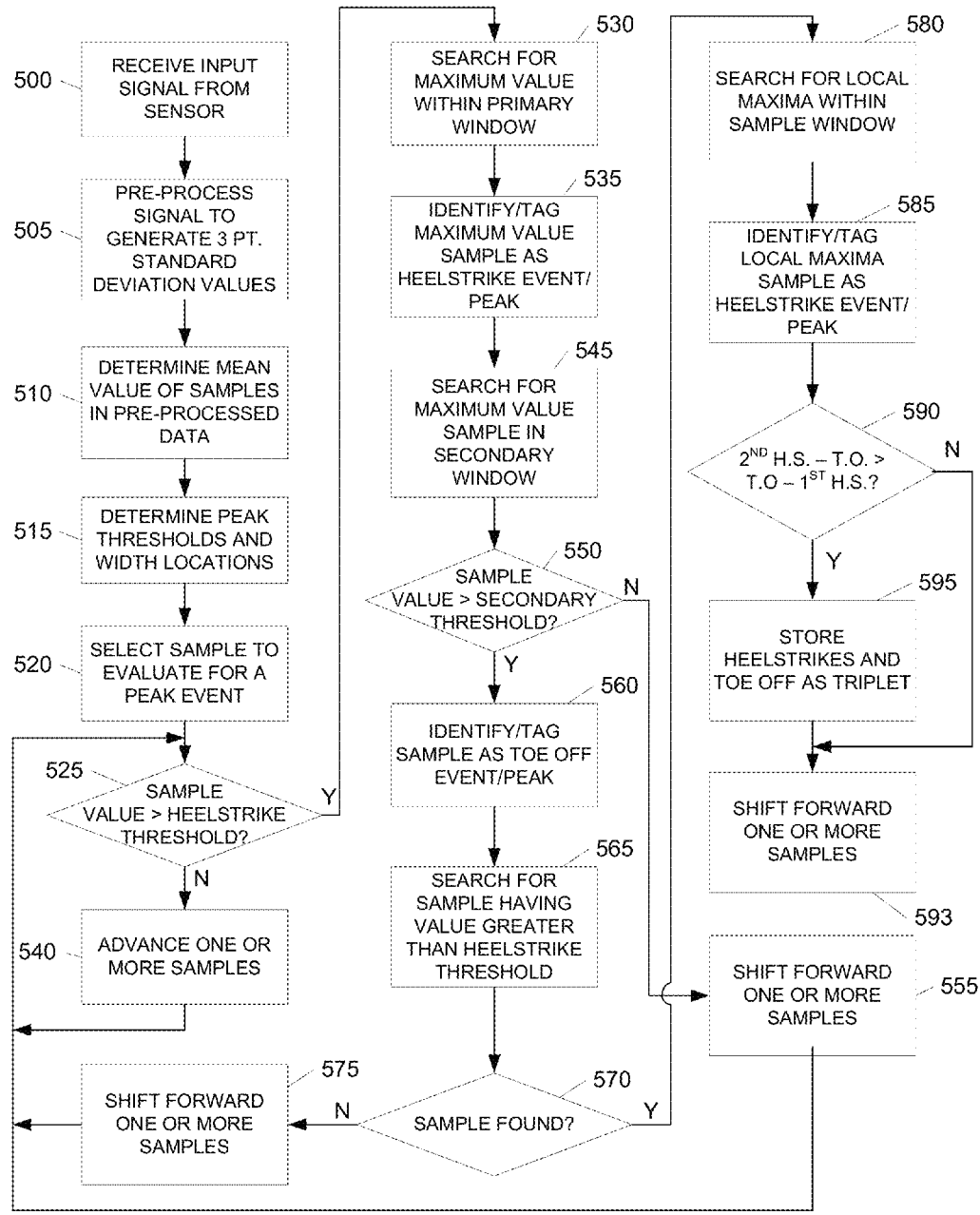
FIG. 5 is a flowchart illustrating an example method for determining athletic events using sensor output data according to one or more aspects described herein.

FIG. 5 illustrates an example method for identifying heelstrike and toe-off events based on an input signal such as a signal generated by an accelerometer or other foot-based sensor. In step 500, a processing system may receive an input signal from a foot-based sensor. For example, the signal may be similar to the signal shown in graph 300 of FIG. 3. The processing system may be integrally formed with the foot-based sensor or include a physically separate device that is wirelessly connected or wired to the sensor. In one example, the processing system may be included as part of a wrist worn, chest worn, head worn, shoulder worn or other body worn device. In step 505, the processing system may pre-process the signal data to generate three point standard deviation values as described above with respect to FIGS. 3 and 4. In step 510, the processing system may subsequently determine the mean value of the samples in the pre-processed data. The mean value may be calculated for all data in the sample set or for a subset of less than all of the data (e.g., only for a particular window in the data). For example, the mean value may be determined for a set including an immediately previous sample value, the current sample value and an immediately subsequent sample value, a set including every other sample value of the entire sample set and the like. Using the determined mean value, the processing system may then determine peak thresholds and width locations in step 515. Width locations may specify the number of samples to shift when searching for a particular peak (e.g., a toe-off peak or a heelstrike peak). The peak thresholds, on the other hand, may define a minimum value that must be met for a sample to be considered a potential heelstrike or toe-off event peak. An example process for determining the peak thresholds and width locations is described in further detail below with respect to FIG. 6.

In step 520, the processing system may select a sample to evaluate for a peak event. For example, upon initiation of the processing, the selected sample may correspond to the first sample in the pre-processed data set. Alternatively, if the processing has already begun, the selected sample may be the next sample in the data set. In step 525, the processing system may determine if the value of the sample is greater than or equal to the heelstrike threshold as determined in step 515. If so, the processing system may search for a maximum value of the heelstrike event within a primary peak sample window in step 530. For example, the processing system may identify the sample having the greatest value within a primary peak sample window of 40-60 samples of the current sample. The primary peak window may be defined as beginning with the current sample and extending forward for a predefined amount of time or number of samples. Once the maximum value is found, the corresponding sample may be identified and tagged as a first heelstrike event or peak in step 535. If, however, the value of the current sample is less than the heelstrike threshold, the processing system may advance one or more samples in step 540 and return to step 525. In one example, the processing system may shift a single sample if the current sample value is less than the heelstrike threshold. In other examples, the processing system may shift multiple samples (e.g., 2, 5, 10, 100, etc.).

Once the heelstrike event has been found within the primary peak sample window, the processing system may search for a sample having the greatest value within a secondary peak sample window in step 545. The size of the secondary peak sample window may be different from or the same as the size of the primary peak sample window and may be calculated according to the algorithms and processes described herein. In one example, the secondary peak sample window may range from 50-220 samples away from the current sample. Accordingly, the processing system may identify the sample having the greatest value within the 50-220 sample window. In step 550, the processing system may determine whether the greatest value identified in the secondary peak sample window is greater than a secondary threshold. The secondary threshold, in one example, may correspond to a threshold for identifying a toe-off event (e.g., a toe-off threshold). If not, the processing system may shift a number of samples forward in step 555 and return to step 525 using the new current sample. The number of samples that the processing system shifts forward may, in one or more arrangements, correspond to the primary peak window size (e.g., 40-60 samples). In other examples, the shift size may correspond to the secondary peak window size (e.g., 50-220 samples) or other sizes (e.g., 10 samples, 1 sample, 25 samples, 500 samples, etc.). If, on the other hand, the greatest value identified in the secondary peak sample window is greater than the secondary threshold, the processing system may identify and tag the corresponding sample as a toe-off event and peak in step 560. Additionally, the processing system may then search for a subsequent sample having a value greater than the primary threshold within a search window of samples away from the toe-off event sample in step 565. The search window may, in one example, be 60-300 samples from the toe-off event sample. If such a value is not found within the search window as determined in step 570, the processing system may shift forward a number of samples in step 575 (e.g., 40-60 samples) and return to step 525. Further, the number of samples shifted in steps 555 and 575 may be the same in one or more configurations.

If, however, a value greater than the primary threshold is found within the search window, the processing system may subsequently identify the local maxima within a local maxima window in step 580. For example, the processing system may compare the values of each sample within the local maxima window of samples to identify the maximum value. The sample corresponding to the maximum value within the local maxima window may then be identified or tagged as a second heelstrike event in step 585. The processing system may thus have identified and tagged a first heelstrike sample/event, a toe-off sample/event and a second heelstrike sample/event identified and tagged upon reaching step 585. To verify and increase the accuracy of the heelstrike and toe-off event identification, the processing system may determine whether the difference between the second heelstrike value and the toe-off value is greater than the difference between the toe-off value and the first heelstrike value in step 590. If not, the processing system may shift forward a number of samples from the second heelstrike sample in step 593. The number of samples that the processing system shifts forward may be within the range defined by the size of the primary peak window, for example, or may correspond to another size.

If, on the other hand, the processing system determines that the difference between the second heelstrike value and the toe-off value is greater than the difference between the toe-off value and the first heelstrike value, the processing system may identify and store the three values and samples as a valid triplet of heelstrike, toe-off and heelstrike events in step 595. In one example, the processing system may store the sample numbers and values in a list of triplet samples and values. Once the sample values have been stored, the processing system may shift forward a number of samples and continue to identify heelstrike and toe-off events (e.g., by returning to step 525). In one example, the number of samples that the processing system shifts after identifying a valid heelstrike, toe-off, heelstrike triplet may range from 50-220 samples. In some arrangements, the number of samples shifted upon identifying a valid triplet may be different from the number of samples shifted in response to determining that a heelstrike or toe-off threshold has not been met (e.g., in steps 540, 555 and 575).

Figure 6:
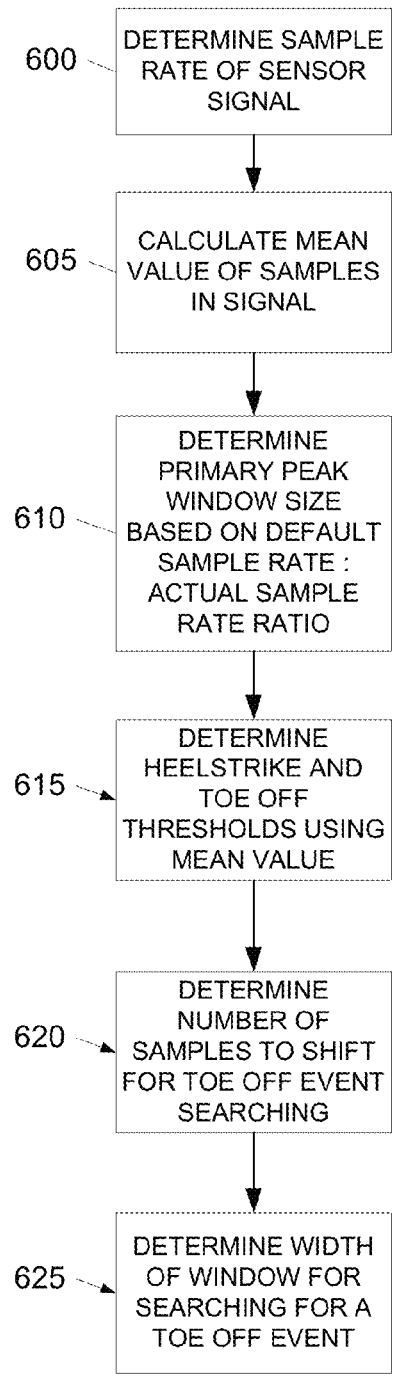
FIG. 6 is a flowchart illustrating an example method for determining various thresholds and window sizes for identifying athletic events according to one or more aspects described herein.

FIG. 6 illustrates a method by which the heelstrike and toe-off thresholds, sample window sizes and shift amounts may be determined. In step 600, a system may determine a sample rate corresponding to a sensor signal. The sensor signal may, for example, correspond to data output by an accelerometer or a pre-processed signal using the standard deviation algorithm described above. In step 605, the system may further calculate a mean value of the samples in the signal. For example, the mean value may be determined in a similar manner as described in step 510 of FIG. 5. In step 610, the system may determine the primary peak window size based on a ratio between a default sample rate (e.g., 400 Hz, 200 Hz, 300 Hz, 50 Hz, 1000 Hz) and an actual sample rate. In one example, the primary peak window size may be calculated according to the following formula:

$$\text{primary peak window size} = \text{round}(z * \text{Default Rate} / \text{Actual Rate})$$

where z corresponds to a constant (e.g., 40) and the round function is used to round the resulting value to the nearest integer. In step 615, the system may further determine a heelstrike and toe-off value threshold based on the mean value. In one example, the heelstrike value threshold is determined as follows:

$$\text{heelstrike threshold} = \text{mean value} + 0.05$$

while the toe-off value threshold may be determined using the formula:

$$\text{toe-off threshold} = 1.1 * \text{mean value} - 0.225$$

In step 620, the system may determine the number of samples to shift for searching for a toe-off event or sample (e.g., as described in step 535 of FIG. 5) based on the ratio of the actual sample rate to the default sample rate as well as the mean value. The shift amount may also be used when a potential heelstrike sample value does not meet a corresponding threshold (e.g., steps 525 and 575 of FIG. 5) and/or after verifying and storing a triplet (e.g., step 593 of FIG. 5). For example, the following formula may be used to calculate the shift amount:

shift amount=round(round(−40*mean value+70)*
(default rate/actual rate))

Finally, in step 625, the system may determine the width of the window for searching for a toe-off event (e.g., as described in step 540 of FIG. 5). Accordingly, a processing system may search for the toe-off event in a window that begins at a sample that is the determined shift amount away from the current sample, where the window has a size equal to the determined window width. For example, the following formula may be used to determine the window width:

window width=round(round(−140*mean value+195)*
(default rate/actual rate))

The above process of dynamically determining the various peak thresholds, shift amounts and window widths may be performed on-the-fly as data is received from or generated by a sensor. For example, the mean value may be continuously determined and the thresholds, shift amounts and window widths updated. In some examples, the process of FIG. 6 may be performed on a periodic or aperiodic schedule such as every 30 seconds, every 10 seconds, every minutes, every 30 minutes, upon prompting by the user, upon detection of a shift in speed, contact time or pace and the like and/or combinations thereof.

Figure 7:
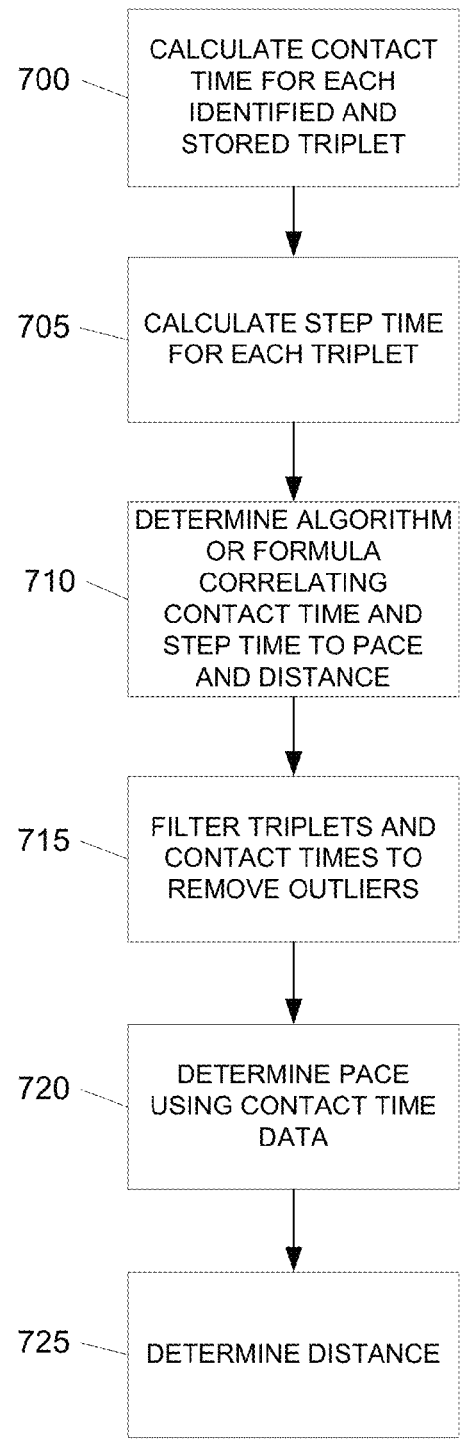
FIG. 7 is a flowchart illustrating an example method for determining contact time, pace and speed according to one or more aspects described herein.

Once the toe-off and heelstrike event peaks have been identified from sensor output signals, a processing system may then determine the contact time and pace of the user as illustrated in FIG. 7. In step 700, for example, a processing system may calculate the contact time ($T_c$) for each triplet (e.g., set of heelstrike, toe-off and heelstrike events) by determining the difference in time between the toe-off event and the first heelstrike event for each triplet, which generally corresponds to the amount of time a user's foot is in contact with the ground. In step 705, the processing system may further calculate the step time ($T_s$) for each triplet. The step time corresponds to the amount of time it takes for a user to take one step (e.g., from heelstrike to subsequent heelstrike event of each triplet). Accordingly, the step time may be determined by measuring the difference in time between the two heelstrike events. In step 710, the processing system may determine and/or select a formula or algorithm that correlates contact time and step time to pace and distance. For example, a linear equation may be developed that specifies a relationship between contact time and pace and/or a correlation of contact time and step time with distance. In one or more arrangements, the formulas or equations may be generated empirically (e.g., through sample studies and data).

In step 715, the processing system may perform a filtering operation that removes triplets exhibiting a contact time that is more than a predefined number of standard deviations away from a mean contact time value. A triplet's corresponding contact time may also be filtered out from the set of calculated contact times. The processing system may filter the data in order to remove potentially inaccurate data that would otherwise skew the processing system's determination of a pace, speed, distance and other metrics. Accordingly, if a contact time falls outside of a particular number of standard deviations (e.g., 1, 2, 5, etc.), the corresponding triplet may be removed from the data set. A pace, contact time, speed and the like for the time period corresponding to the removed triplet may be determined by interpolating between accepted or non-removed triplets. Additionally, the processing system may check to insure that the athlete did not simply stop. In one example the processing system may determine whether any acceleration was detected during that time. For example, if there was acceleration, then the processing system may determine that the user did not stop. If there was no acceleration, then the processing system may determine that the user stopped. The mean contact time value may be determined over a specified number of steps or contact times rather than the entire set of contact times that is available. For example, the mean may be calculated based on the last 5-10 steps. Similarly, the standard deviations may be calculated based on the same range of steps or contact times.

Figure 8:
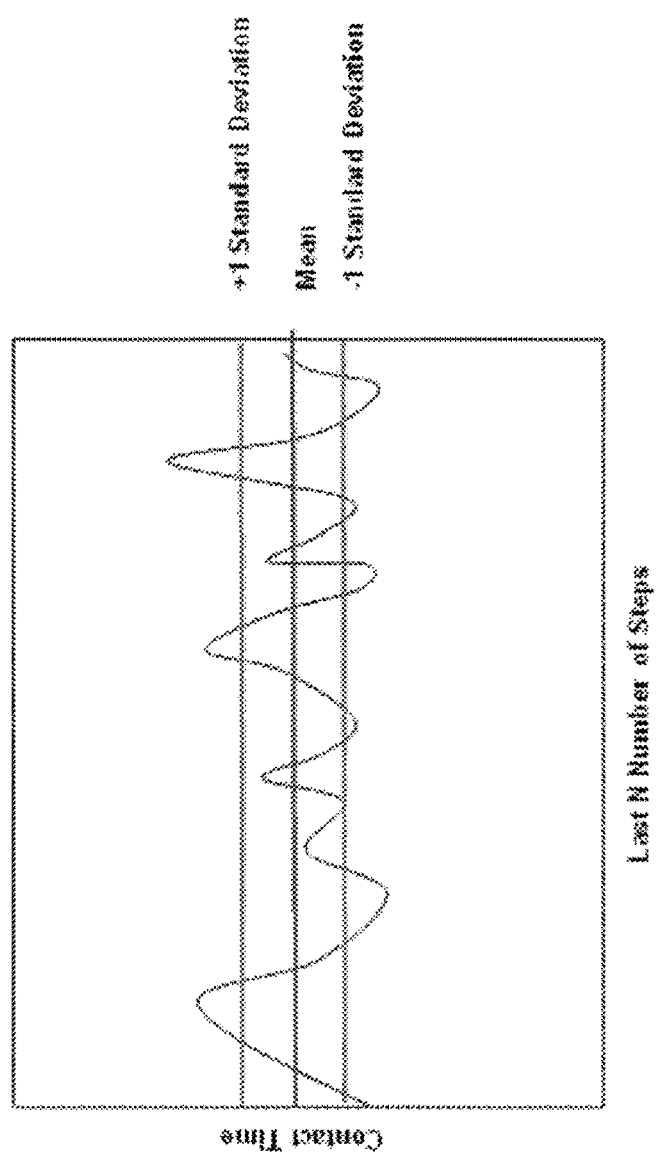
FIG. 8 illustrates example standard deviations and a mean for a set of data according to one or more aspects described herein.

FIG. 8 illustrates an example graph of contact time versus step or triplet number. As indicated in the graph, the mean is initially determined for the last N number of steps of triplets. Subsequently, corresponding thresholds for a number of standard deviations (e.g., 1) may be determined and contact times and corresponding triplets may be filtered out of the data based on the relevant standard deviations.

Referring again to FIG. 7, once filtering has been completed, the processing system may subsequently calculate or otherwise determine pace using the remaining contact time data in step 720. Pace may be calculated based on a predefined linear relationship with contact time. For example, the relationship may be governed by the equation:

$$\text{Pace}=M*T_c+B$$

where M and B are constants defining the slope and Y-intercept of the linear relationship. M and B may be determined empirically, in one example, through sample data. M and B may further be adjusted based on calibrations performed by the user. Different types of pace may also be calculated. For example, an instantaneous pace may be determined based on a single contact time, while an average pace over a predefined amount of time or steps may be determined based on the contact times resulting from the predefined amount of time or steps. Thus, in one example, the processing system may calculate an average contact time over the last minute to determine a person's average pace over that time period. Additionally, from pace, distance may be calculated in step 725. For example, pace may be multiplied by the amount of time to determine a total distance that the user ran or walked or otherwise moved.

According to one or more aspects, the relationship between pace and contact time may be non-linear. Accordingly, in such cases, a non-linear equation may be derived to describe the relationship. For example, a quadratic relationship may be defined and used to interpret pace from contact time.

In addition or as an alternative to determining contact time using triplet detection as described herein, contact time may also be determined based on frequency and empirical analyses. In particular, a signal received from a sensor such as an accelerometer may be processed using a Fast Fourier Transform (FFT) to determine the frequency range represented within the signal and the strength of those frequencies.

Figure 9:
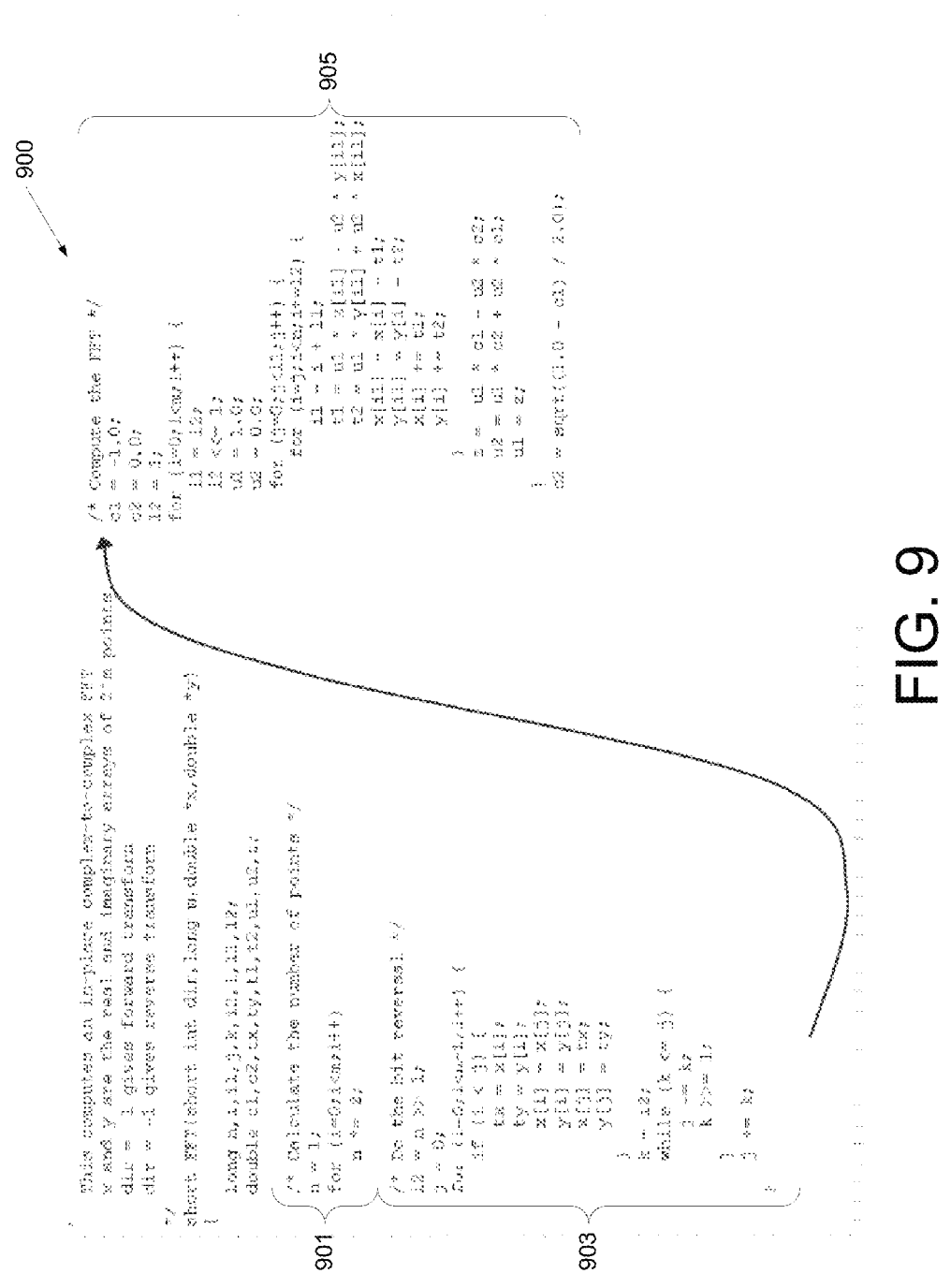

FIG. 9 illustrates an example computer algorithm that may be used to perform an FFT process on a received signal. This example algorithm was retrieved from DFT/FFT (written by Paul Bourke, http://paulbourke.net/miscellaneous/dft. As noted, the algorithm initially calculates a number of sample points based on value m as shown in section 901 of algorithm 900. The value 'm' corresponds to the $\log_2$ of the number of samples while x and y represent the real and imaginary arrays of the sample points, respectively. Once the number of data points has been determined, a bit reversal process is performed for each data point as shown in section 903. For example, a value of 1 may be represented by the 4-bit binary expression "0001." Upon bit reversal, the value of that data point (originally 0001) may be converted into "1000" (representing a value of 8). After performing the bit reversal for each of the sample points in the x and y arrays, the algorithm computes the FFT using, for example, the formulas and processes illustrated in section 905.

FIG. 10A illustrates an example sensor signal produced from a sprinting session. In one arrangement, the sensor signal may correspond to a sampling rate of 75 Hz. From the complete sensor signal, a sample window 1001 may be extracted as shown in FIG. 10B. Due to the number of peaks and samples, even the extracted sample window may be difficult to interpret in determining a contact time. Accordingly, an FFT may be performed on the sample window. The FFT used may include the algorithm discussed above with respect to FIG. 9.

Figure 11:
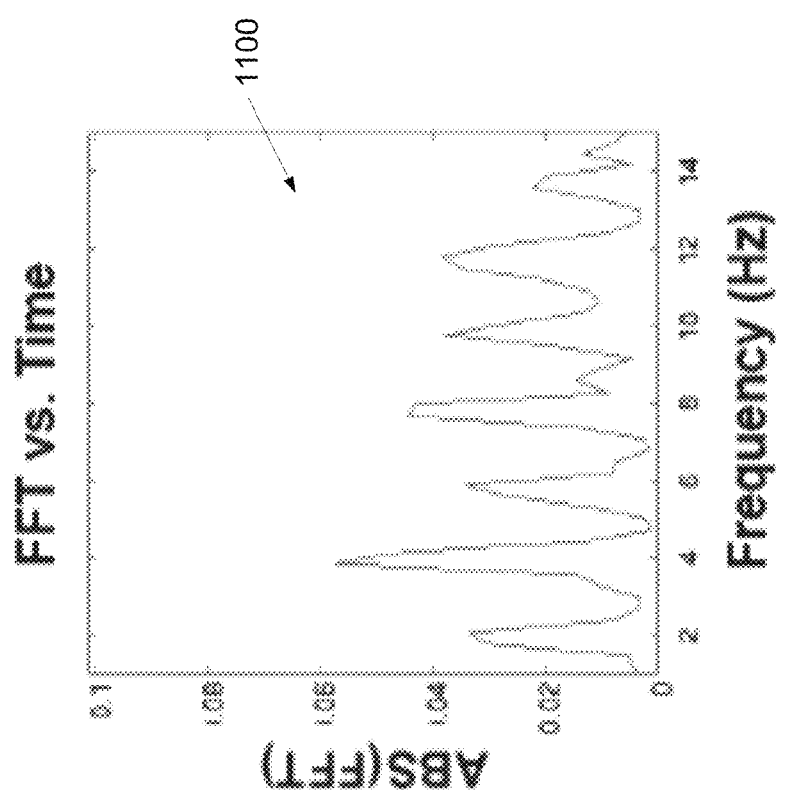
FIG. 11 is graph of the sample window of FIG. 10B processed by a FFT algorithm.

FIG. 11 illustrates an FFT v. Frequency graph 1100 that may be produced based on the FFT of the sample window of data. From this graph 1100, a frequency corresponding to the contact time may be determined. In one example, the frequency may be determined empirically based on multiple signal samples. In a particular example, a contact time for a sample signal output may be determined by viewing and timing video of the run corresponding to the sample signal output. Upon determining the contact time, a user may then manually identify a frequency corresponding to the determined contact time. Frequency may include the frequency of waves to which the acceleration data is matched. For example, the act of a runner's foot contacting the ground and then pushing off and going into the air and back down to the ground may generate accelerations that can be fit with a suitable fitting function (e.g., sine and cosine waves). The frequency of these waves may directly correspond to the characteristic times the athlete's foot was active or performing some activity.

The above described process may be repeated to determine if a pattern or rule may be established to identify the appropriate frequency from an FFT graph such as graph 1100. For instance, the sample studies may indicate that the third lowest frequency peak generally corresponds to the contact time. Accordingly, a processing system may automatically identify the third lowest frequency peak in FFT v. Frequency graph 1100 as the frequency corresponding the contact time.

Figures 12A, 12B, 12C:
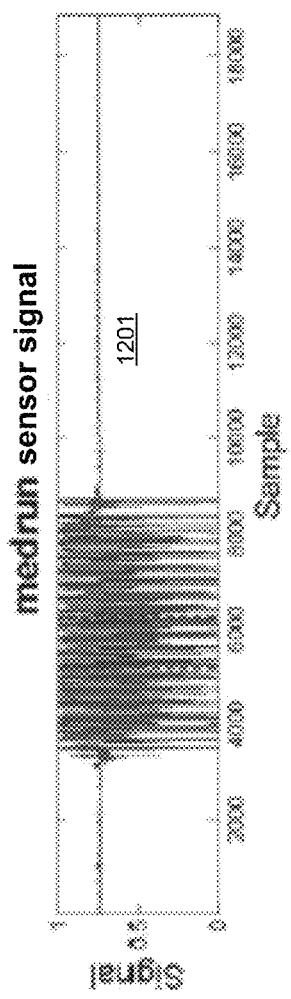
FIGS. 12A-12C illustrate example sensor output data and corresponding graphs of a sample window and a FFT processed sample window according to one or more aspects described herein.

FIGS. 12A-12C are example graphs illustrating the FFT processing of a sensor output signal to determine a frequency peak corresponding to contact time. In particular, graphs 1201-1205 may correspond to a sensor output signal, a corresponding sample window and a corresponding FFT frequency graph, respectively, for a medium paced run (e.g., a run below a specified pace or speed threshold) versus the sensor output signal corresponding to a sprint illustrated in FIGS. 10A, 10B and 11.

According to yet another arrangement, an athlete's speed may be determined or calculated based on a moving average of the sensor output signal. The determination may be based on a correlation or relationship between speed or pace and the value of the sensor output signal. The sensor output signal may represent an amount of effort set forth by the athlete.

Figure 13A:
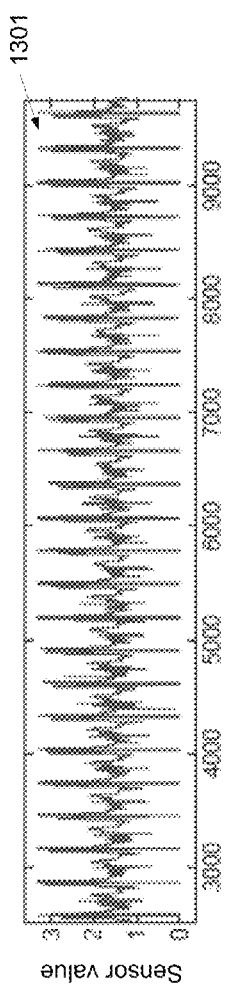
FIGS. 13A-13C illustrate example sensor output data graphs for different speeds of user movement according to one or more aspects described herein
Figure 13B:
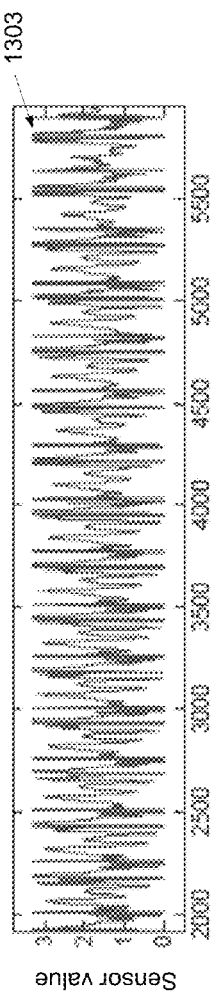
Figure 13C:
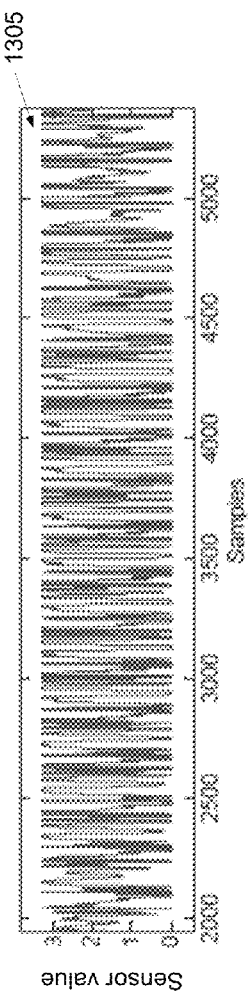

FIGS. 13A-13C are graphs illustrating a difference in amount of sensor output data generated when an athlete is running or walking at different paces or speeds. For example, FIG. 13A illustrates graph 1301 in which an athlete is moving at a first pace or speed that may be considered a slow jog (e.g., 5 mph or 6 mph). Visually, graph 1301 illustrates a significant amount of non-signal space (e.g., represented by the white space in contrast to the dark lines representing the signal output). In FIG. 13B, graph 1303 shows the signal output of an athlete moving at a second, faster pace relative to the first pace. In one example, the sensor output signal of graph 1303 may correspond to a fast jog (e.g., 8 mph, 10 mph, 11 mph). Due to the greater speed or pace of the athlete, more data is generated based on the athlete's movement. Accordingly, graph 1303 exhibits less non-signal space (e.g., less white space as compared to the amount of white or non-signal space of graph 1301 of FIG. 13A). FIG. 13C shows graph 1305 illustrating signal output data for an even faster pace. This faster pace may correspond to a sprint in one example and may thus result in an even greater amount of sensor output. As such, the pace may be determined by generating a linear correlation between the amount or magnitude of output data received from an athletic sensor (e.g., an accelerometer) and pace. For example, a higher average sensor output value over a sample window may represent a higher level of activity and thus, a faster pace or speed.

Figure 14A:
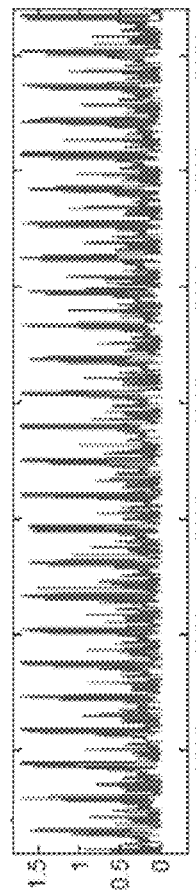
FIGS. 14A-14C illustrate example mean-centered data graphs for the sensor output illustrated in FIGS. 13A-13C, respectively.
Figure 14B:
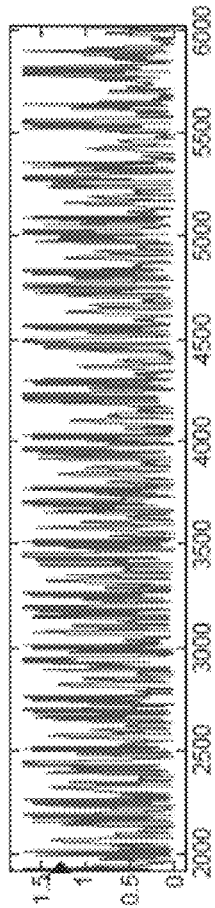
Figure 14C:
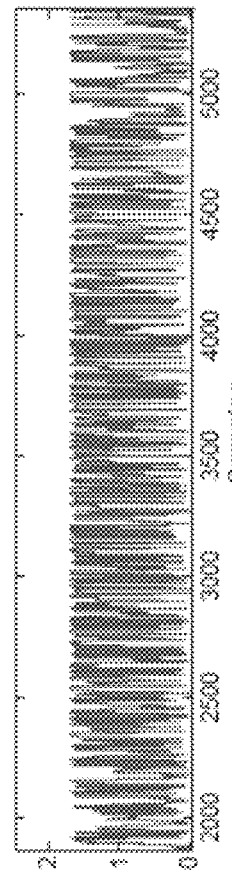

In some arrangements, a processing system may preliminarily process the sensor output data to generate mean-centered sensor data. For example, a mean value may be calculated for a given sample period in the sensor output and subsequently subtracted from each of the data points in the sample period. FIGS. 14A-14C are graphs illustrating mean-centered sensor data corresponding to the sensor output graphs of FIGS. 13A-13C, respectively. Mean centering allows a signal to fluctuate from negative to positive values. Using the absolute value of these values allows for the calculation of the overall mean acceleration an athlete is producing. For example, the absolute value may reflect how much effort or acceleration someone is producing. If the mean of a non-mean centered signal is taken, the result may be the baseline acceleration value which will generally be the same for all different running speeds. Accordingly, by using mean centering, fake low frequency content may be removed or eliminated and an athlete's level of effort may be more accurately determined. In one arrangement, the mean for a specified sample window may be determined based on the following formula:

$$meanvalue = \left(\frac{1}{t_f - t_o}\right)\int_{t_o}^{t_f} f(t)\,dt = \left(\frac{1}{\#\,samples * h}\right) \sum_{i=1}^{\#samples-1} (f_i + f_{i+1})\left(\frac{h}{2}\right)$$

where $t_f$ and $t_o$ represent the upper and lower sample bounds of the sample window, respectively, h represents an amount of time represented by one data sample (or a time span from the last sample) and f(t) represents the sensor output value corresponding to the particular sample. For example, if the sample rate is 100 Hz, h would represent 0.01 seconds. In another example, if the sample rate is 400 Hz, h would represent 0.0025 seconds.

Using either the original sensor output or the mean-centered sensor output (or both), a linear relationship between effort and pace may be applied to determine either instantaneous or average pace for a particular point in time or time period. As described herein, the linear relationship may be empirically predefined based on sample sensor output. In one or more arrangements, different linear relationships may be defined for different speeds or paces of movement. For example, a first linear relationship or equation may be used for walking. A processing system may determine that sensor output or a portion thereof represents walking based on threshold values or average values of the sensor output. Thus, different linear equations or relationships may be selected for different levels of running or movement.

Figure 15:
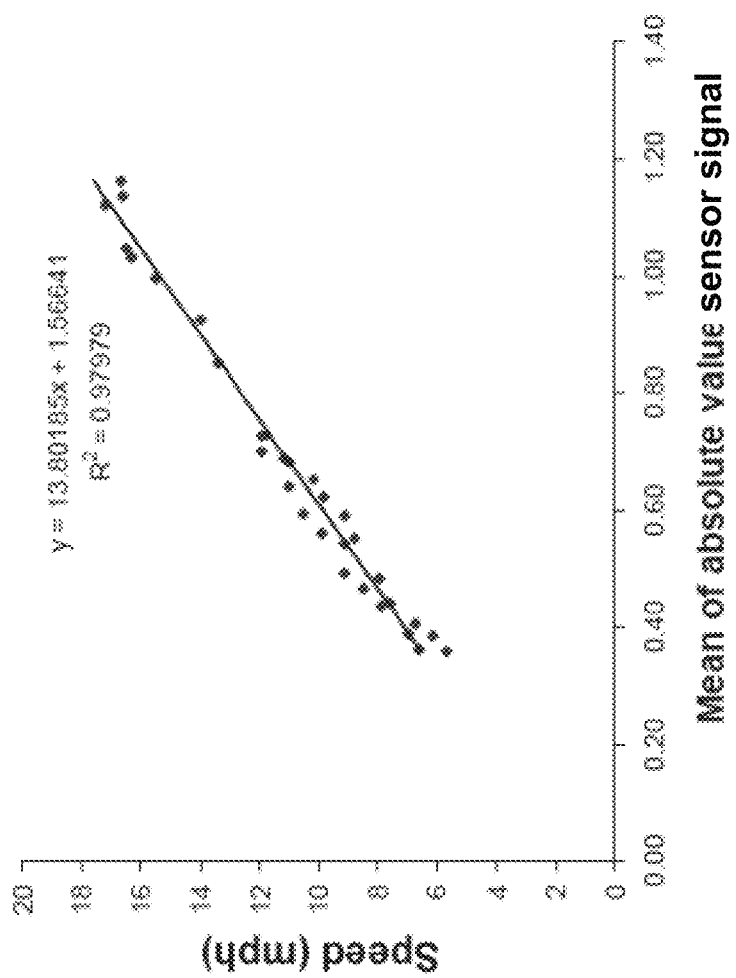
FIG. 15 illustrates a graph showing a relationship between a mean value of sensor output and speed for a first type of movement according to one or more aspects described herein.

FIG. 15 is a graph illustrating sample sensor values and their relationship to known speeds for running activities (e.g., movement speeds at or above 6 mph). Based on the sample data, the linear relationship may be generated (e.g., y=13.80185x+1.56641). This linear relationship may then be used by the processing system to determine speed values on-the-fly as sensor output is received during a user's athletic activity.

Figure 16:
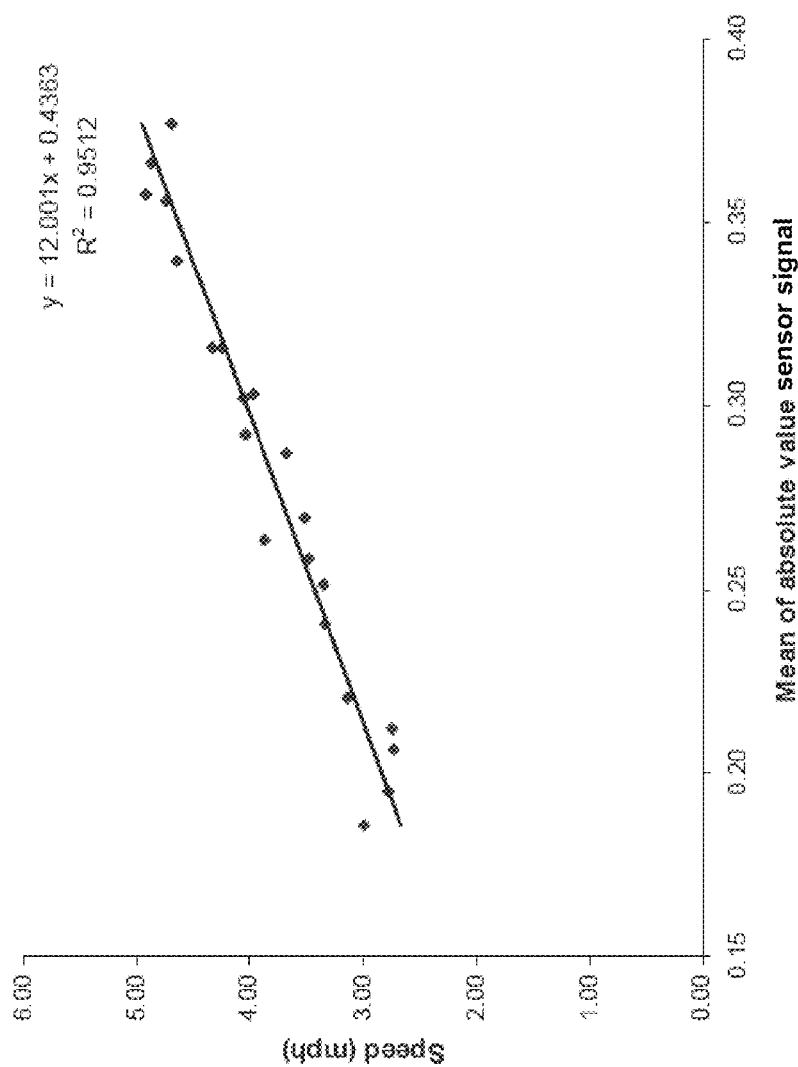
FIG. 16 illustrates a graph showing a relationship between a mean value of sensor output and speed for a second type of movement according to one or more aspects described herein.

FIG. 16 is a graph illustrating sample sensor values and their relationship to known speeds of walking activities (e.g., movement speeds below 6 mph). The linear relationship between speed and sensor output for walking activities is determined in this example to be y=12.001x+0.4363. Accordingly, if a user's movement corresponds to walking, this linear relationship may be used instead of the one defined using the data of FIG. 15. In some arrangements, pace and sensor output values may be related in a non-linear manner. As such, one or more non-linear equations (e.g., quadratic) may be defined and used instead.

The various methods and algorithms described herein may be used together or separately. In one example, the pace and speed of a user may be determined using the triplet methodology, the FFT algorithm as well as the effort algorithm. The user's speed or pace may be determined by averaging the paces and speeds determined from the various algorithms, respectively. Alternatively, a first algorithm may be used to determine a pace or speed and a second algorithm may be applied to confirm the determination. For example, a determined pace or speed may be confirmed so long as the second algorithm generates a value that is sufficiently similar. Sufficient similarity may correspond to a percentage threshold such as with 10%, 20%, 5%, etc. of the initially calculated value or a predefined amount (e.g., 0.5 mph, 0.2 mph, 0.3 mph, etc.)

While the specific embodiments have been illustrated and described, numerous modifications come to mind without significantly departing from the spirit of the invention and the scope of protection is only limited by the scope of the accompanying Claims.

What is claimed is:

1. A method comprising:
    receiving a signal generated by a foot-based sensor during athletic activity performed by a user, wherein the signal comprises a plurality of samples;
    processing the signal based on a rolling standard deviation;
    identifying, from the rolling standard deviation processed signal, a sequence of three samples in the signal that corresponds to a physical foot-step taken by the user, wherein the sequence of three samples includes a first heelstrike sample, a toe-off sample and a second heelstrike sample;
    determining a pace of the user based on an elapsed time between at least two of the first heelstrike, toe-off and second heelstrike samples; and
    responsive to having received a user request to determine a pace during the athletic activity, providing the determined pace to a user display device.

2. The method of claim 1, further comprising:
    determining a first difference between a value of the second heelstrike sample and a value of the toe-off sample;
    determining a second difference between a value of the toe-off sample and the value of the first heelstrike sample;
    determining whether the first difference is greater than the second difference; and
    in response to determining that the first difference is greater than the second difference, adding the sequence of three samples to a list.

3. The method of claim 2, further comprising:
    adding a plurality of three sample sequences to the list; and
    determining a plurality of contact times of the user based on the plurality of three sample sequences in the list.

4. The method of claim 3, further comprising:
    determining a mean contact time of the plurality of contact times;
    determining a standard deviation between the plurality of contact times; and
    filtering out one or more contact times of the plurality of contact times that exceed a threshold number of standard deviations from the mean contact time.

5. The method of claim 1, wherein determining the pace of the user based on an elapsed time between at least two of the first heelstrike, toe-off and second heelstrike samples includes:
    determining a contact time by determining a difference between the toe-off sample and the first heelstrike sample;
    selecting a predefined linear relationship from a plurality of linear relationships, wherein each of the plurality of linear relationships corresponds to a different type of athletic activity; and
    applying the predefined linear relationship to the contact time to calculate the pace of the user.

6. The method of claim 1, wherein identifying the sequence of three samples in the signal that corresponds to a physical foot-step taken by the user includes:
    selecting a first sample from the plurality of samples;
    determining whether a value of the first sample is at or above a first threshold sample value;
    in response to determining that the value of the first sample is not at or above the first threshold sample value, selecting a subsequent sample in the plurality of samples; and
    in response to determining that the value of the first sample is at or above the first threshold sample value:
        determining a maximum sample value in a first sample window of a predefined size, wherein a lower bound of the first sample window corresponds to the first sample, and
        identifying a sample corresponding to the maximum sample value as the first heelstrike sample.

7. The method of claim 6, wherein in response to determining that the value of the first sample is at or above the first threshold sample value, the method further comprises:
    determining a maximum sample value in a second sample window; and
    determining whether the maximum sample value of the second sample window is at or above a second threshold sample value; and
    in response to determining that the maximum sample value of the second sample window is at or above the second threshold sample value, identifying a sample corresponding to the maximum sample value of the second sample window as the toe-off sample.

8. The method of claim 1, wherein the rolling standard deviation includes a plurality of standard deviations corresponding to the plurality of samples.

9. The method of claim 1, wherein the rolling standard deviation is calculated using an equation as follows:

$$\sigma_i = \sqrt{\left(\frac{1}{N}\sum_{i=1}^{i+1}(x_i - \bar{x}_i)^2\right)}$$

wherein N represents a number of samples being considered, i represents a sample number, x represents a raw signal output value, $\bar{x}$ represents a mean raw signal output of the number of samples being considered.

10. An apparatus comprising:
a foot-based sensor;
at least one processor; and
one or more non-transitory computer readable media coupled to the at least one processor and storing computer readable instructions that, when executed, cause the apparatus to:
receive a signal generated by the foot-based sensor during athletic activity performed by a user, wherein the signal comprises a plurality of samples;
process the signal based on a rolling standard deviation;
identify, from the rolling standard deviation processed signal, a sequence of three samples in the signal that corresponds to a physical foot-step taken by the user, wherein the sequence of three samples includes a first heelstrike sample, a toe-off sample and a second heelstrike sample;
determine a pace of the user based on an elapsed time between at least two of the first heelstrike, toe-off and second heelstrike samples; and
responsive having received a user request to determine a pace during the athletic activity, provide the determined pace to a user display device.

11. The apparatus of claim 10, wherein the one or more non-transitory computer readable media contains further computer readable instructions that, when executed, cause the apparatus to:
determine a first difference between a value of the second heelstrike sample and a value of the toe-off sample;
determine a second difference between a value of the toe-off sample and the value of the first heelstrike sample;
determine whether the first difference is greater than the second difference; and
in response to determining that the first difference is greater than the second difference, adding the sequence of three samples to a list.

12. The apparatus of claim 11, wherein the one or more non-transitory computer readable media contains further computer readable instructions that, when executed, cause the apparatus to:
add a plurality of three sample sequences to the list; and
determine a plurality of contact times of the user based on the plurality of three sample sequences in the list.

13. The apparatus of claim 12, wherein the one or more non-transitory computer readable media contains further computer readable instructions that, when executed, cause the apparatus to:
determine a mean contact time of the plurality of contact times;

determine a standard deviation between the plurality of contact times; and
filter out one or more contact times of the plurality of contact times that exceed a threshold number of standard deviations from the mean contact time.

14. One or more non-transitory computer readable media storing computer readable instructions that, when executed, cause an apparatus to:
receive a signal generated by a foot-based sensor during athletic activity performed by a user, wherein the signal comprises a plurality of samples;
process the signal based on a rolling standard deviation;
identify, from the rolling standard deviation processed signal, a sequence of three samples in the signal that corresponds to a physical foot-step taken by the user, wherein the sequence of three samples includes a first heelstrike sample, a toe-off sample and a second heelstrike sample; and
determine a pace of the user based on an elapsed time between at least two of the first heelstrike, toe-off and second heelstrike samples and
responsive to having received a user request to determine a pace during the athletic activity, provide the determined pace to a user display device.

15. The one or more non-transitory computer readable media of claim 14, wherein determining the pace of the user based on an elapsed time between at least two of the first heelstrike, toe-off and second-heelstrike samples includes:
determining a contact time by determining a difference between the toe-off sample and the first heelstrike sample;
selecting a predefined linear relationship from a plurality of linear relationships, wherein each of the plurality of linear relationships corresponds to a different type of athletic activity; and
applying the predefined linear relationship to the contact time to calculate the pace of the user.

16. The one or more non-transitory computer readable media of claim 14, wherein identifying the sequence of three samples in the signal that corresponds a physical foot-step taken by the user includes:
selecting a first sample from the plurality of samples;
determining whether a value of the first sample is at or above a first threshold sample value;
in response to determining that the value of the first sample is not at or above the first threshold sample value, selecting a subsequent sample in the plurality of samples; and
in response to determining that the value of the first sample is at or above the first threshold sample value:
determining a maximum sample value in a first sample window of a predefined size, wherein a lower bound of the first sample window corresponds to the first sample, and
identifying a sample corresponding to the maximum sample value as the first heelstrike sample.

17. The one or more non-transitory computer readable media of claim 14, further comprising computer readable instructions that, when executed, cause the apparatus to:
determine a first difference between a value of the second heelstrike sample and a value of the toe-off sample;
determine a second difference between a value of the toe-off sample and the value of the first heelstrike sample;
determine whether the first difference is greater than the second difference;

in response to determining that the first difference is greater than the second difference, add the sequence of three samples to a list;

add a plurality of three sample sequences to the list; and determine a plurality of contact times of the user based on the plurality of three sample sequences in the list.

* * * * *